United States Patent
Jackson et al.

(10) Patent No.: US 7,084,272 B2
(45) Date of Patent: Aug. 1, 2006

(54) PROCESS FOR THE PREPARATION OF AZOXYSTROBIN AND ANALOGUES THEREOF

(75) Inventors: David Anthony Jackson, Muenchwilen (CH); James Peter Muxworthy, Huddersfield (GB); Mark Robert Sykes, Huddersfield (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 10/480,863

(22) PCT Filed: May 3, 2002

(86) PCT No.: PCT/GB02/02078

§ 371 (c)(1),
(2), (4) Date: Jun. 9, 2004

(87) PCT Pub. No.: WO02/100837

PCT Pub. Date: Dec. 19, 2002

(65) Prior Publication Data

US 2004/0242607 A1    Dec. 2, 2004

(30) Foreign Application Priority Data

Jun. 13, 2001   (GB)  ................. 0114408.8

(51) Int. Cl.
*C07D 239/52*   (2006.01)
(52) U.S. Cl. ..................................... 544/319
(58) Field of Classification Search ................. 544/319
See application file for complete search history.

(56) References Cited

U.S. PATENT DOCUMENTS 5,395,837 A   3/1995  Clough et al.

FOREIGN PATENT DOCUMENTS

| EP | 0242081 | 10/1987 |
|---|---|---|
| WO | 9701538 | 1/1997 |
| WO | 9730020 | 8/1997 |

OTHER PUBLICATIONS

Solladie-Cavallo, Arlette; Csaky, Aurelio, G.; Gantz, Ingo; Suffer, Jean: "Diastereoselective Alkylation of 8-Phenylmenthyl Phenylacetate: Aggregated Lithium Enolate versus "Naked" Enolate" J. Org. Chem. vol. 59, 1994, pp. 5343-5346.
*Advanced Organic Chemistry* by Jerry March, 4th Edition, pp. 675-676, published by John Wiley & Sons, 1992.
*Organic Chemistry*, vol. 1, by I.L. Finar, 3rd Ed., 1959; p. 629.

*Primary Examiner*—Deepak Rao
(74) *Attorney, Agent, or Firm*—Rebecca Gegick

(57) ABSTRACT

A process for the preparation of a compound of the general formula (I): wherein $R^1$ is a 4-pyrimidinyl ring substituted at the 6-position by halo, hydroxy, 2-cyanophenoxy, 2,6-difluorophenoxy, 2-nitrophenoxy or 2-thiocarboxamidophenoxy and $R^2$ is any group which can be transesterified to form a methyl ester, which comprises treating a compound of general formula (II): wherein $R^1$ and $R^2$ have the meanings given above, with a formylating agent and subsequently treating the formylated product with a methylating agent

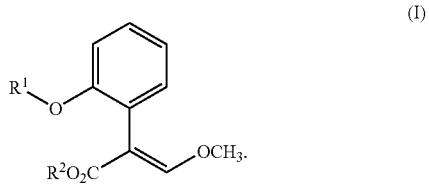

(I)

3 Claims, 2 Drawing Sheets

PROCESS FOR THE PREPARATION OF AZOXYSTROBIN AND ANALOGUES THEREOF

This invention relates to a process for the preparation of the agricultural fungicide azoxystrobin and analogues thereof, and to chemical intermediates therefor. It also relates to processes for making the chemical intermediates and to their use for making other chemical compounds.

The strobilurin fungicide methyl (E)-2-{2-[6-(2-cyanophenoxy)pyrimidin-4-yloxy]phenyl}-3-methoxyacrulate, known by the common name azoxystrobin, is a widely used commercial agrochemical product. It is described in The Pesticide Manual published by the British Crop Protection Council, 12$^{th}$ edition, pp 54–55 and in the proceedings of the Brighton Crop Protection Conference (Pests and Diseases) 1992, Volume 1, 5–6, pp 435–442. It was first disclosed in EP-A-0382375 (compound 9, Example 3) along with methods for its preparation.

There are many ways of making azoxystrobin. Generally, it is preferred to construct the methyl α-phenyl-β-methoxyacrylate group at an early stage and then build on the central pyrimidinyloxy and terminal cyanophenoxy rings. For example, (E)-methyl 2-(2-hydroxyphenyl)-3-methoxyacrylate may be reacted with 4,6-dichloropyrimidine under alkaline conditions in N,N-dimethylformamide to form (E)-methyl 2-[2-(6-chloropyrimidin-4-yloxy)phenyl)-3-methoxyacrylate which is then reacted with 2-cyanophenol in an Ullmann-type coupling process (see EP-A-0382375). The (E)-methyl 2-(2-hydroxyphenyl)-3-methoxyacrylate may be prepared by the formylation and subsequent methylation of methyl 2-benzyloxyphenylacetate followed by removal of the benzyl protecting group (see EP-A-0242081). Formylation and methylation techniques for preparing the methyl α-phenyl-β-methoxyacrylate warhead are also described in WO 97/30020 and WO 97/01538.

One reason for constructing the methyl α-phenyl-β-methoxyacrylate group before building on the central pyrimidinyloxy ring is that, with the pyrimidinyloxy ring in place, methyl 2-(6-chloropyrimidin-4-yloxy)phenylacetate and methyl 2-[6-(2-cyanophenoxy)pyrimidin-4-yloxy]phenylacetate are prone to undergo a Smiles-type intramolecular rearrangement when the usual bases for conducting the formylation and methylation stages are used to form the methyl methoxyacrylate group. Smiles rearrangements are discussed in the textbook *Advanced Organic Chemistry* by Jerry March, 4$^{th}$ edition, pp 675–676, published by John Wiley & Sons. In the case of the methyl 2-[6-(2-cyanophenoxy)pyrimidin-4-yloxy]phenylacetate, the compound obtained as a result of a Smiles rearrangement has the formula:

or its keto tautomeric form.

The present invention, which involves the use of a lithium base, provides a method of constructing the methyl α-phenyl-β-methoxyacrylate group after building on the central pyrimidinyloxy ring or the central pyrimidinyloxy ring and terminal cyanophenol ring. It avoids a Smiles-type rearrangement and delivers the desired E-isomer.

It is known to use lithiated bases for the monoalkylation of 8-phenylmenthyl phenylacetate (see *J Org Chem*, 1994, 59, 5343–5346). It is also known to prepare substituted benzaldehydes by heating a substituted phenyl-lithium compound with ethyl orthoformate or N-methylformanilde and hydrolysing with acid the intermediate compound so formed (see, for example, *Organic Chemistry*, vol 1, by I L Finar, 3$^{rd}$ edition, 1959, p 629). There is no indication, however, that lithiated bases could be successfully employed in the formylation and subsequent methylation of 2-pyrimidinyloxy substituted phenyl acetates in order to convert the acetate group to the E-isomer of methyl α-phenyl-β-methoxyacrylate group.

Figure 1:
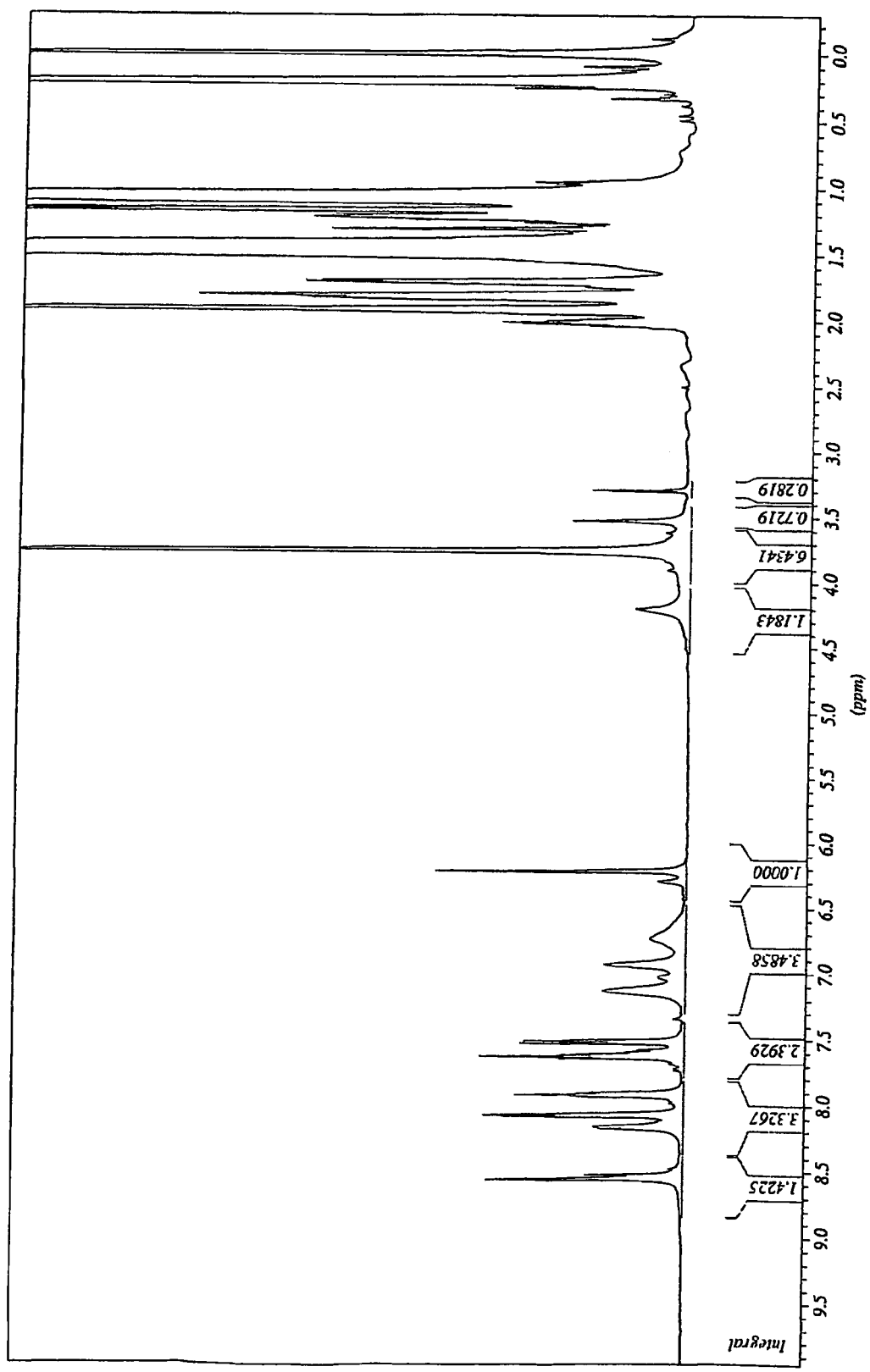
FIG. 1 is a proton NMR spectrum of the product in Example 5.

According to the present invention there is provided a process for the preparation of a compound of the general formula (I):

wherein $R^1$ is a 4-pyrimidinyl ring substituted at the 6-position by halo (especially chloro), hydroxy, 2-cyanophenoxy, 2,6-difluorophenoxy, 2-nitrophenoxy or 2-thiocarboxamidophenoxy and $R^2$ is any group which can be transesterified to form a methyl ester, which comprises treating a compound of general formula (II):

wherein $R^1$ and $R^2$ have the meanings given above, with a formylating agent and subsequently treating the formylated product with a methylating agent.

The process is of particular interest where $R^1$ is a 4-pyrimidinyl ring substituted at the 6-position by chloro or 2-cyanophenoxy.

The term halo includes fluoro, chloro, bromo and iodo. When used in the context of the definition of $R^1$ as a substituent in the 6-position of a 4-pyrimidinyl ring, it is preferably chloro.

The group $R^2$ is suitably a $C_{1-8}$ alkyl group or a benzyl or phenyl group in which the phenyl rings are unsubstituted or may carry one or more substituents compatible with the susceptibility of the group to be transesterified into a methyl group. Most conveniently $R^2$ is methyl.

Except where otherwise stated, alkyl groups will normally contain from 1 to 8, typically from 1 to 6, for example 1 to 4, carbon atoms in the form of straight or branched chains. Specific examples are methyl, ethyl, n- and iso-propyl, n-, sec-, iso- and tert-butyl, n-pentyl, n-hexyl and n-octyl.

Suitable formylating agents include those of general formula $R^1O$—CHO, wherein $R^1$ is an aliphatic group containing from 1 to 8 carbon atoms, typically a $C_{1-4}$ alkyl group, or an optionally substituted aromatic group, for example, an optionally substituted phenyl group such as 4-nitrophenyl. Other suitable formylating agents include N-disubstituted formamides, such as N-methylformanilide, and N-formylimidazole.

Suitable methylating agents are compounds of the general formula MeL wherein Me is methyl and L is a good leaving group such as a halide. Methyl iodide is particularly suitable.

The treatment is conveniently carried out in an organic solvent, suitably an aprotic solvent, at a temperature between −80° C. (approximately the temperature achieved using dry ice, i.e. solid carbon dioxide, for cooling) and 25° C. (the upper end of the 'ambient temperature' range). The formylation step is suitably carried out at a temperature between −80° C. and −40° C., preferably −78° C. and −60° C. The methylation step can be carried higher temperatures, suitably at a temperature between −20° C. and 25° C., for example between −10° C. and 10° C., typically at about 0° C.

Examples of aprotic solvents are ethers such as diethyl ether, tetrahydrofuran, glyme (1,2-dimethoxyethane) and diglyme (the dimethyl ether of diethylene glycol), 1-methyl-2-pyrrolidinone, tetramethylenediamine and dimethylformamide. Tetrahydrofuran and glyme are particularly suitable.

Because of the unsymmetically substituted double bond of its vinylic group, the compound of general formula (II) may exist in the form of a mixture of the (E) and (Z) geometric isomers:

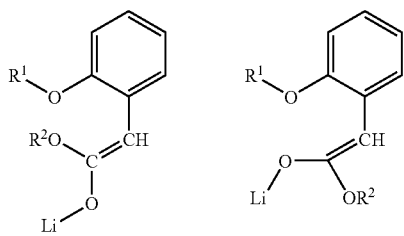

It may also exist in the form of its tautomer:

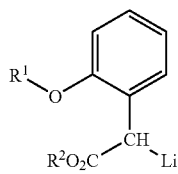

It is believed that one of the (E)- and (Z)-isomers predominates greater than 90%, but this invention embraces both the (E)- and (Z)-isomers, the tautomeric form and mixtures thereof in all proportions, including those which consist substantially of the (E)-isomer and those which consist substantially of the (Z)-isomer.

The general formula (II) is, therefore, to be read as including the (E)- and (Z)-isomers and the tautomer, either individually or as any mixtures thereof.

The compound of general formula (II), which is a novel compound and forms another aspect of the present invention, may be prepared by treating a compound of general formula (III):

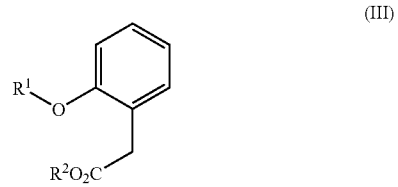

wherein $R^1$ and $R^2$ have the meanings given above, with a lithium base.

Suitable lithium bases include those of general formula R'R"NLi wherein R' and R" are independently an aliphatic group containing from 1 to 8 carbon atoms, typically a $C_{1-4}$ alkyl group, or an optionally substituted aromatic group, for example, an optionally substituted phenyl group. A particularly suitable lithium base of this type is lithium diisopropylamide. Another suitable lithium base is lithium bis(trimethylsilyl)amide.

The compound of the general formula (III) may be prepared as described in EP-A-0382375 and EP-A-0242081.

The treatment is conveniently carried out in an organic solvent, suitably an aprotic solvent, at a temperature between −80° C. and 40° C., preferably −78° C. and −60° C. Examples of aprotic solvents are given above.

This process for preparing the compound of general formula (II) forms another aspect of the present invention.

Conveniently the two processes, viz. the formation of the lithium compound (II) and the conversion of compound (II) to the compound (I), can be carried out in a 'one pot' process using the same solvent medium.

Typically, a solution of the 2-substituted phenylacetate (III) in a dry aprotic solvent is cooled to −78° C. and the lithium base added with stirring. This is followed by addition of the formylating agent and stirring is continued at around this temperature. After allowing the temperature to rise to about 0° C., the methylating agent is added and the mixture stirred at ambient temperature until no further reaction takes place. The product (compound (I)) may be isolated by drowning the mixture into water and extracting the product with a solvent such as dichloromethane. The extract is dried and the product isolated by removing the solvent by evaporation.

Thus, according to another aspect of the invention, there is provided a process for the preparation of a compound of the general formula (I):

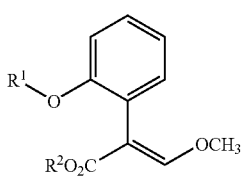

(I)

wherein $R^1$ is a 4-pyrimidinyl ring substituted at the 6-position by halo (especially chloro), hydroxy, 2-cyanophenoxy, 2,6-difluorophenoxy, 2-nitrophenoxy or 2-thiocarboxamidophenoxy and $R^2$ is any group which can be transesterified to form a methyl ester, which comprises the steps:

(a) treating a compound of general formula (III):

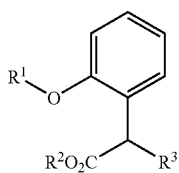

(III)

wherein $R^1$ and $R^2$ have the meanings given above, with a lithium base; and (b) treating the compound so formed with a formylating agent and subsequently treating the formylated product with a ethylating agent.

The processes of the invention are useful for preparing the agricultural fungicide azoxystrobin and analogues thereof and for preparing intermediate products for conversion into azoxystrobin or analogues thereof. In the case where $R^2$ is other than methyl, $R^2$ may be converted to methyl by standard transesterification techniques described in the chemical literature.

As well as being useful as an intermediate for conversion to the compound (I), the compound of general formula (II) may also be used for conversion to related compounds by reaction with other electrophiles.

Thus according to yet another aspect of the present invention, there is provided a process for the preparation of a compound of general formula (IV):

(IV)

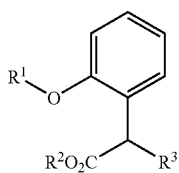

wherein $R^1$ is a 4-pyrimidinyl ring substituted at the 6-position by halo (especially chloro), hydroxy, 2-cyanophenoxy, 2,6-difluorophenoxy, 2-nitrophenoxy or 2-thiocarboxamidophenoxy, $R^2$ is any group which can be transesterified to form a methyl ester and $R^3$ is an alkyl or acyl group, which comprises treating a compound of general formula (II):

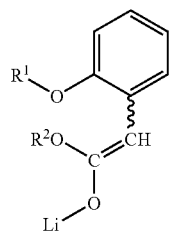

(II)

wherein $R^1$ and $R^2$ have the meanings given above, with an alkylating or acylating agent.

Suitable allylating agents include those compounds of the general formula $R^3X$ wherein $R^3$ is $C_{1-4}$ alkyl and X is chloro, bromo or iodo. Methyl iodide is particularly suitable.

Suitable acylating agents include those compounds of the general formula $R^3COX'$, wherein $R^3$ is an aliphatic group containing from 1 to 8 carbon atoms, typically a $C_{1-4}$ alkyl group, or an optionally substituted aromatic group, for example, an optionally substituted phenyl group, and X' is fluoro, chloro or bromo. Acetyl chloride is particularly suitable.

The treatment is conveniently carried out in an organic solvent, suitably an aprotic solvent, at a temperature between −80° C. and 25° C. Examples of aprotic solvents are given above. Suitably the alkylating or acylating agent is added at a temperature between −80° C. and −40° C., preferably −78° C. and −60° C., and the reaction mixture then allowed to warm to ambient temperature.

This process for preparing the compound of general formula (IV) forms another aspect of the present invention.

Conveniently the two processes, viz. the formation of the lithium compound (II) and the conversion of compound (II) to the compound (IV), can be carried out in a 'one pot' process using the same solvent medium.

Typically, a solution of the 2-substituted phenylacetate (III) in a dry aprotic solvent is cooled to −78° C. and the lithium base added with stirring. This is followed by addition of the alkylating or acetylating agent and stirring is continued while allowing the temperature to rise to ambient. The product (compound (IV)) may be isolated by drowning the mixture into saturated ammonium chloride and extracting the product with a solvent such as dichloromethane. The extract is dried and the product isolated by removing the solvent by evaporation.

Thus, according to yet another aspect of the invention, there is provided a process for the preparation of a compound of the general formula (IV):

(IV)

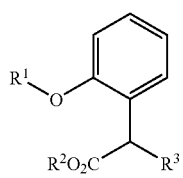

wherein $R^1$ is a 4-pyrimidinyl ring substituted at the 6-position by halo (especially chloro), hydroxy, 2-cyanophenoxy, 2,6-difluorophenoxy, 2-nitrophenoxy or 2-thiocarboxamidophenoxy, $R^2$ is any group which can be transesterified to form a methyl ester and $R^3$ is an alkyl or acyl group, which comprises the steps:

(a) treating a compound of general formula (III):

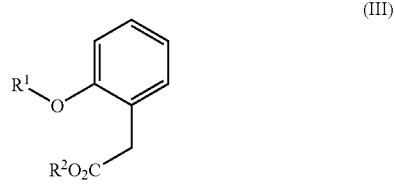

(III)

wherein $R^1$ and $R^2$ have the meanings given above, with a lithium base; and (b) treating the compound so formed with an alkylating or acylating agent.

In the case where $R^2$ in the compound of general formula (IV) is other than methyl, it may be converted to methyl by standard transesterification techniques described in the chemical literature.

The invention is illustrated by the following Examples in which g=grammes
mol=moles
w/w=weight/weight
GC-MS=gas chromatography-mass spectometry
HPLC=high performance liquid chromatography
IR=infra-red
THF=tetrahydrofuran
ml=millilitres
NMR=nuclear magnetic resonance
°C.=degrees centigrade

EXAMPLE 1

This Example illustrates the preparation of methyl (E)-2-{2-[6-(2-cyanophenoxy)pyrimidin-4-yloxy]phenyl}-3-methoxyacrylate (azoxystrobin)

Anhydrous tetrahydrofuran (2 ml) was added to methyl 2-[6-(2-cyanophenoxy)pyrimidin4-yloxy]phenylacetate (0.10 g at 95% w/w, $2.63 \times 10^{-4}$ mol; prepared as described in Example 4) in a round-bottomed flask under a dry inert atmosphere. The solution was agitated well and cooled to −78° C. A solution of lithium bis(trimethylsilyl)amide in tetrahydrofuran (0.28 ml, 1 mol/l, $2.84 \times 10^{-4}$ mol) was added, followed by 4-nitrophenylformate (0.46 g at 98%, $2.71 \times 10^{-3}$ mol). The solution was stirred at −78° C. for 30 minutes then allowed to warm to 0° C. and stirred for 3 hours. Iodomethane (1 ml, 0.016 mol) was added to the solution at 0° C. and the mixture was stirred for 16 hours at room temperature.

The reaction mixture was drowned into water and extracted with dichloromethane (3×15 ml). The organic extracts were combined, dried over magnesium sulphate and concentrated by rotary evaporation to give a pale yellow solid (0.5 g). 4-Nitrophenol and 4-nitrophenylformate were identified as the major components by NMR and GC-MS. A peak representing approximately 2% by GC-MS area had a retention time and mass spectra consistent with azoxystrobin. Yield 10% (based on area %).

EXAMPLE 2

This Example illustrates the preparation of methyl 2-{2-[6-(2-cyanophenoxy)pyrimidin-4-yloxy]phenyl}propanoate Anhydrous tetrahydrofuran (2 ml) was added to methyl 2-[6-(2-cyanophenoxy)pyrimidin-4-yloxy]phenyl acetate (0.21 g at 94% w/w, $5.54 \times 10^{-4}$ mol; prepared as described in Example 4) in a round-bottomed flask under a dry inert atmosphere. The solution was agitated well and cooled to −78° C. A solution of lithium bis(trimethylsilyl)amide in tetrahydrofuran (0.55 ml, 1 mol/l $5.54 \times 10^{-4}$ mol) was added followed by iodomethane (0.10 ml, $1.61 \times 10^{-3}$ mol). The solution was allowed to warm to room temperature. The reaction mixture was drowned into saturated ammonium chloride (10 ml) and extracted with dichloromethane (3×15 ml). The organic extracts were combined, dried over magnesium sulphate and concentrated by rotary evaporation to give a pale, brown oil (0.2 g). NMR and GC-MS spectra were consistent with methyl 2-{2-[6-(2-cyanophenoxy)pyrimidin-4-yloxy]phenyl}propanoate. Yield>95%.

EXAMPLE 3

This Example illustrates the preparation of methyl 2-[6-(2-cyanophenoxy)pyrimidin-4-yloxy]phenylacetoacetate Anhydrous tetrahydrofuran (2 ml) was added to methyl 2-[6-(2-cyanophenoxy)pyrimidin-4-yloxy]phenylacetate (0.1 g at 94% w/w, $2.6 \times 10^{-4}$ mol; prepared as described in Example 4) in a round-bottomed flask under a dry inert atmosphere. The solution was agitated well and cooled to −78° C. A solution of lithium bis(trimethylsilyl)amide in tetrahydrofuran (0.26 ml, 1 mol/l, $2.6 \times 10^{-4}$ mol) was added followed by acetyl chloride (0.05 ml, $7 \times 10^{-4}$ mol). The mixture was stirred at −78° C. for 1.5 hours then the solution was allowed to warm to room temperature overnight. The reaction mixture was drowned into saturated ammonium chloride (10 ml) and extracted with dichloromethane (3×15 ml). The organic extracts were combined, dried over magnesium sulphate and concentrated by rotary evaporation to give a yellow oily solid (0.1 g at 49% purity). NMR and GC-MS spectra were consistent with the product being methyl 2-[6-(2-cyanophenoxy)pyrimidin-4-yloxy]phenylacetoacetate. Yield 44%.

EXAMPLE 4

This Example illustrates the preparation of the methyl 2-[6-(2-cyanophenoxy)pyrimidin-4-yloxy)phenylacetate used in Examples 1, 2 and 3.

Stage 1: Preparation of methyl 2-(6-chloropyrimidin-4-yloxy)phenyl acetate

Methyl 2-hydroxyphenylacetate (54.7 g, 0.3295 mol) and 4,6 dichloropyrimidine (50.0 g at 97% w/w strength, 0.3295 mol) were dissolved and stirred in dimethylformamide (50 ml) under a dry nitrogen atmosphere. Potassium carbonate (81.8 g) was added and the mixture was heated to 50° C. and held for 2.5 hours. Completion of reaction was checked by gas chromatography.

The reaction mixture was allowed to cool then filtered through a bed of pre-washed celite. The celite was rinsed with dimethylformamide to remove residual product. A sample was taken and partitioned between water and cyclohexane. The organic phase was dried over magnesium sulphate and concentrated by rotary evaporation to give a pale yellow oil. The oil was analysed by GC-MS and proton NMR.

The combined dimethylformamide solution of product was returned to the flask for use in the next stage.

Stage 2: Preparation of methyl 2-[6-(2-cyanophenoxy)pyrimidin-4-yloxy]phenylacetate 2-Cyanophenol (43.1 g, 0.3625 mol) was added to the stirred solution of the Stage 1 product (91.4 g, 0.3295 mol) in dimethylformamide. Extra dimethylformamide (50 ml) was added followed by potassium carbonate (68.2 g). The mixture was heated to 120° C., held for 20 minutes then cooled to 80° C.

Dimethylformamide was removed by vacuum distillation to a vacuum of 20 mmHg and batch temperature of 100° C. The melt was cooled to 80° C. before adding toluene (210 ml) followed by hot water (200 ml). The mixture was re-heated to 80° C. and stirred for 30 minutes. Agitation was then stopped and the mixture was allowed to stand for 30 minutes. The lower two layers were run from the vessel leaving the upper toluene phase behind. Toluene was removed by vacuum distillation to a vacuum of 20 mmHg and batch temperature of 100° C. The residue was allowed to cool to <65° C.

The residue was refluxed in 120 ml methanol to dissolve then allowed to cool to 40° C. and stirred for 4 hours before cooling to 0° C. holding for 1 hour then leaving to stand for 64 hours at room temperature. The crystals were filtered, displacement washed with 2×25 ml methanol then pulled dry by vacuum. Product yield from methyl 2-hydroxyphenylacetate was 23.7% theory. The product identity of the Stage 2 title product was confirmed by GC-MS and proton NMR spectroscopy.

EXAMPLE 5

This Example characterises and illustrates the stability of lithiated methyl 2-[6-(2-cyanophenoxy)pyrimidin-4yloxy]phenylacetate (Compound II where $R^1$ is 6-(2-cyanophenoxy)pyrimidin-4-yl and $R^2$ is methyl)

Methyl 2-[6-(2-cyanophenoxy)pyrimidin-4-yloxy]phenylacetate (17.2 mg at 100% w/w, 4.76×10⁻⁵ mol; prepared as described in Example 4) was weighed into an NMR tube and dissolved in tetrahydrofuran, d8 (0.75 ml, anhydrous). The solution was cooled to –70° C. using an acetone/solid carbon dioxide bath. Lithium bis(trimethylsilyl)amide solution (95 µl of 1 mol/litre solution in hexanes, 9.53×10⁻⁵ mol) was added and the solution was well mixed. Proton NMR spectra were taken periodically using a 500 MHz instrument at –70° C. over 2 hours.

The solution was quenched at –70° C. with glacial acetic acid (50 µl, 8.3×10⁻⁴ mol) and mixed well. The quenched solution was mixed with 5 ml water and extracted with dichloromethane (2×10 ml). The organics were combined, dried over magnesium sulphate and concentrated by rotary evaporation. The residue was analysed by reverse phase HPLC using UV/V is detection and also by proton NMR. The proton NMR spectrum is shown in FIG. 1.

In FIG. 1, signals at ~0–2.5 are attributable to the lithium bis(trimethylsilyl)amide and hexanes. Proton signals that correspond to the methoxy and methylene groups in the neutral methyl 2-[6(2-cyanophenoxy)pyrimidin-4-yloxy]phenylacetate were absent in all spectra of the basic solution at –70° C. A singlet at δ6.2 with an integral representing 1 proton was observed and is consistent with the olefinic proton in the anionic species. Changes to all the signals in the aromatic and aliphatic region were also evident. The ratio of both the aromatic and aliphatic signals to the residual tetrahydrofuran signal (internal standard) was constant throughout the two hour period. No other signals were formed or depleted throughout the experiment suggesting the stability of the anion to be in excess of 2 hours at –70° C.

HPLC and NMR data for the quenched material were consistent with methyl 2-[6-(2-cyanophenoxy)-pyrimidin4-yloxy]phenylacetate (>97%).

EXAMPLE 6

Figure 2:
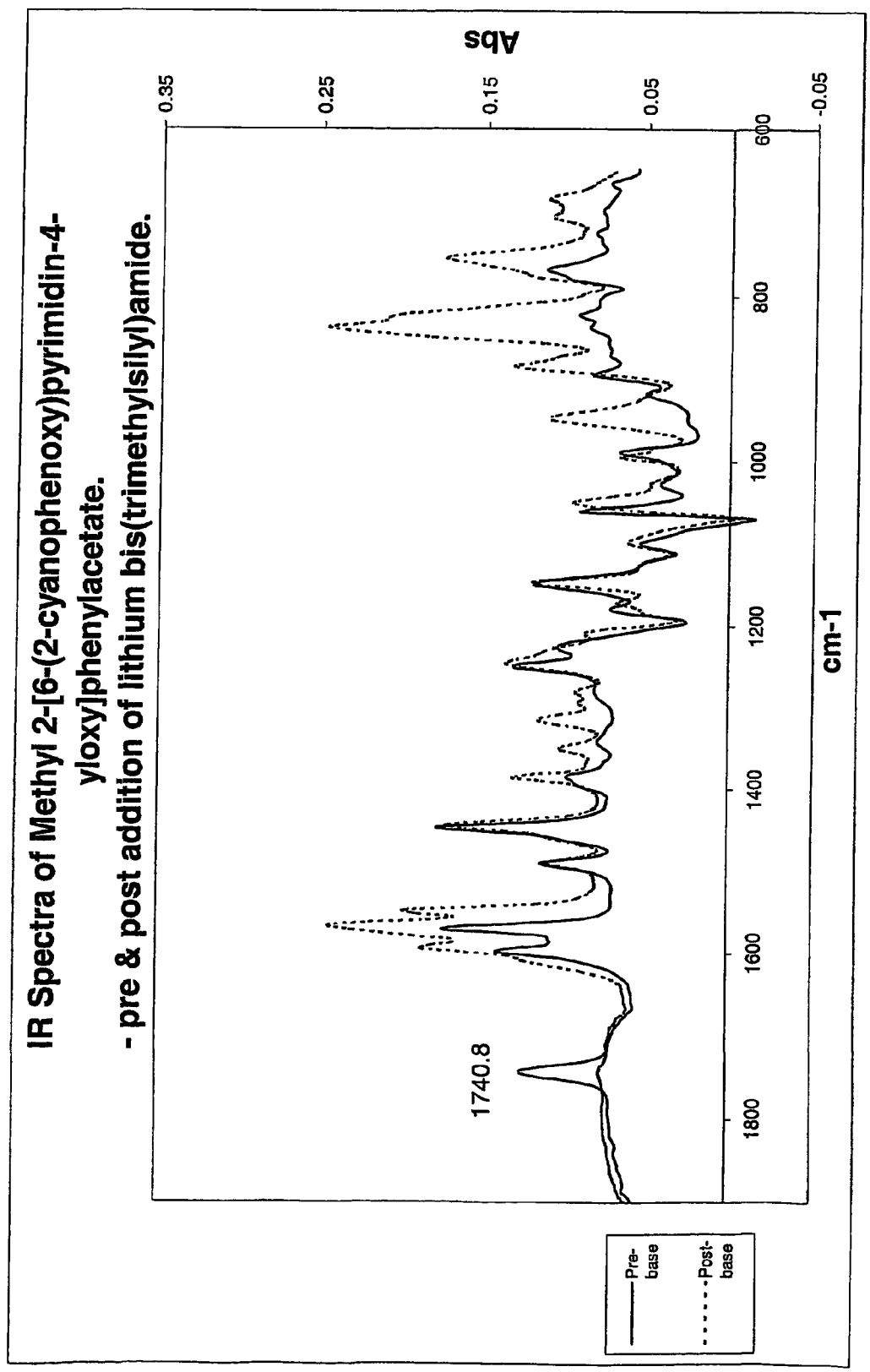
FIG. 2 is an Infra-red spectra of methyl 2-[6-(2-cyanophenoxy)pyrimidin-4-yloxy]phenylacetate before and after the addition of lithium bis(trimethylsilyl)amide.

This Example characterises lithiated methyl 2-[6-(2-cyanophenoxy)pyrimidin-4-yloxy]phenylacetate (Compound II where $R^1$ is 6-(2-cyanophenoxy)pyrimidin-4-yl and $R^2$ is methyl) by its infra-red spectrum Infra-red spectra in TBF at –70° C. were produced for methyl 2-[6-(2-cyanophenoxy)pyrimidin-4-yloxy]phenylacetate before and after the addition of lithium bis(trimethylsilyl)amide (see FIG. 2).

In FIG. 2, it can be seen that the carbonyl stretching band at 1740 cm⁻¹ is not present when methyl 2-[6-(2-cyanophenoxy)pyrimidin-4-yloxy]phenylacetate is treated with lithium bis(trimethylsilyl)amide.

The invention claimed is:

1. A process for the preparation of a compound of the general formula (I):

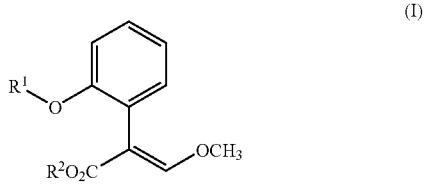

(I)

wherein $R^1$ is a 4-pyrimidinyl ring substituted at the 6-position by halo, hydroxy, 2-cyanophenoxy, 2,6-difluorophenoxy, 2-nitrophenoxy or 2-thiocarboxamidophenoxy and $R^2$ is methyl or any group which can be transesterified to form a methyl ester, which comprises treating a compound of general formula (II):

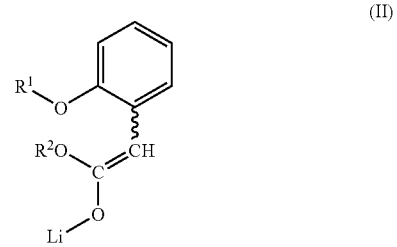

(II)

wherein $R^1$ and $R^2$ have the meanings given above, with a formylating agent and subsequently treating the formylated product with a methylating agent.

2. A process according to claim 1 in which the compound of general formula (I) is azoxystrobin.

3. A process according to claim 1 in which the compound of general formula (I) is (E)-2-[2-(6-chloropyrimidin-4-yloxy)phenyl]-3-methoxyacrylate.

* * * * *